United States Patent [19]
Johnson et al.

[11] Patent Number: 5,574,008
[45] Date of Patent: Nov. 12, 1996

[54] BIOLOGICALLY ACTIVE FRAGMENTS OF GLUCAGON-LIKE INSULINOTROPIC PEPTIDE

[75] Inventors: William T. Johnson; Fatima E. Yakubu-Madas, both of Indianapolis, Ind.

[73] Assignee: Eli Lilly and Company, Indianapolis, Ind.

[21] Appl. No.: 297,731

[22] Filed: Aug. 30, 1994

[51] Int. Cl.$^6$ .......................... A61K 38/00; A61K 38/26; C07K 14/605

[52] U.S. Cl. ........................... 514/12; 530/308; 530/324; 514/866

[58] Field of Search ................................. 530/303, 308, 530/324; 514/3, 2, 12, 13, 14, 866; 435/69.1, 69.4

[56] References Cited

U.S. PATENT DOCUMENTS

| | | | |
|---|---|---|---|
| 5,118,666 | 6/1992 | Habener | 514/12 |
| 5,120,712 | 6/1992 | Habener | 514/12 |
| 5,512,549 | 4/1996 | Chen et al. | 514/12 |

FOREIGN PATENT DOCUMENTS

| | | | |
|---|---|---|---|
| 0082731 | 12/1982 | European Pat. Off. | |
| 0619322A2 | 2/1994 | European Pat. Off. | 7/34 |
| WO87/06941 | 11/1987 | WIPO | |
| WO90/11296 | 10/1990 | WIPO | |
| WO91/11457 | 8/1991 | WIPO | |
| WO93/18786 | 9/1993 | WIPO | 37/28 |
| WO93/25579 | 12/1993 | WIPO | |

OTHER PUBLICATIONS

Granott, D. et al., *Digestion*, 55(5):302, 1994.

Kreymann, et al., "Glucagon–Like Peptide 7–36 A Physiological Incretin In Man", *The Lancet*, vol. 2, pp. 1300–1303 (Dec. 5, 1987).

Holst, et. al., "Truncated glucagon–like peptide I, an insulin-–releasing hormone from the distal gut", *FEBS Letters*, vol. 211, No. 2, pp. 169–174 (Jan. 1987).

Mojsov, et. al., "Insulinotropic: Glucagon–like Peptide I (7–37) Co.–encoded in the Glucagon Gene Is a Potent Stimulator of Insulin Release in the Perfused Rat Pancreas", *The American Society for Clinical Investigation, Inc.*, vol. 79, pp. 616–619 (Feb. 1987).

Goke, et. al., "Glucagon like peptide–1 (7–36) amide is a new incretin/enterogastrone candidate", *European Journal of Clinical Investigation*, vol. 21, pp. 135–144 (1991).

Suzuki, et. al., "Effects Of GLP–1 And Its Fragment Peptides On Pancreatic Hormone Release", *Diabetes Research and Clinical Practice*, Supp. 1, vol. 5, ORA–007–007, p. S30 (1988).

Weir, et. al., "Glucagonlike Peptide I (7–37) Actions on Endocrine Pancreas", *Diabetes*, vol. 38, pp. 338–342 (Mar. 1989).

Komatsu, et. al., "Glucagonostatic and Insulinotropic Action of Glucagonlike Peptide I–(7–36)–Amide", *Diabetes*, vol. 38, pp. 903–905, (Jul. 1989).

Orskov, et. al., "Complete Sequences of Glucagon–like Peptide–1 from Human and Pig Small Intestine", *The Journal of Biological Chemistry*, vol. 264, No. 22, pp. 12826–12929, (Aug. 5, 1989).

Takahashi, et. al., "Radioimmunoassay For Glucagon–Like Peptide–1 In Human Plasma Using N–Terminal And C–Terminal Directed Antibodies: A Physiologic Insulinotropic Role of GLP–1 (7–36 Amide)", *Biomedical Research* vol. 11 (2), pp. 99–108, (1990).

Mojsov, "Structural requirements for biological activity of glucagon–like peptide–I", *Int J Peptide Protein Res*, vol. 40, pp. 333–343 (1992).

Orskov, "Glucagon–like peptide–1, a new hormone of the entero–insular axis", *Diabetologia*, vol. 35, pp. 701–711 (1992).

Thorens, et. al., "Glucagon–Like Peptide–I and the Control of Insulin Secretion in the Normal State and in NIDDM", *Diabetes*, vol. 42, pp. 1219–1225 (Sep. 1992).

Nauck, et. al., "Normalization of fasting hyperglycaemia by exogenous glucagon–like peptide 1 (7–36 amide in Type 2 (non–insulin–dependent) diabetic patients", *Diabetologia*, vol. 36, pp. 741–744 (1993).

Nauck, et. al., "Preserved Incretin Activity of Glucagon–like Peptide 1 (7–36 Amide) but Not of Synthetic Human Gastric Inhibitory Polypeptide in Patients with Type–2 Diabetes Mellitus", *The American Society for Clinical Investigation, Inc.*, vol. 91, pp. 301–307, (Jan. 1993).

Hvidberg, et. al., "Effect of Glucagon–like Peptide–1 (proglucagon 78–107 amide) on Hepatic Glucose Production in Healthy Man", *Metabolism*, vol. 43, No. 1, pp. 104–108, (Jan. 1994).

Suzuki, S., et al. "Comparison of the Effects of Various C–Terminal and N–Terminal Fragment Peptides of Glucagon–Like Peptide–1 on Insulin and Glucagon Release from the Isolated Perfused Rat Pancreas" *Endocrinology*, vol. 125, No. 6, 3109–3114 (1989).

*Primary Examiner*—Marianne P. Allen
*Attorney, Agent, or Firm*—Ronald S. Maciak; David E. Boone

[57] ABSTRACT

N-terminal truncated forms of glucagon like insulinotropic peptide (GLP-1) and analogs thereof are provided. The claimed polypeptides promote glucose uptake by cells but do not stimulate insulin expression or secretion. The invention also provides methods for treating diabetes and pharmaceutical formulations comprising the claimed polypeptides.

22 Claims, No Drawings

BIOLOGICALLY ACTIVE FRAGMENTS OF GLUCAGON-LIKE INSULINOTROPIC PEPTIDE

FIELD OF INVENTION

The present invention relates to medicinal chemistry and provides novel peptides and compositions thereof that are useful for treating diabetes.

BACKGROUND OF THE INVENTION

Endocrine secretions of pancreatic islets are regulated by complex control mechanisms driven not only by blood-borne metabolites such as glucose, amino acids, and catecholamines, but also by local paracrine influences. The major pancreatic islet hormones, glucagon, insulin and somatostatin, interact with specific pancreatic cell types (A, B, and D cells, respectively) to modulate the secretory response. Although insulin secretion is predominantly controlled by blood glucose levels, somatostatin inhibits glucose-mediated insulin secretion.

The human hormone glucagon is a 29-amino acid hormone produced in pancreatic A-cells. The hormone belongs to a multi-gene family of structurally related peptides that include secretin, gastric inhibitory peptide, vasoactive intestinal peptide and glicentin. These peptides variously regulate carbohydrate metabolism, gastrointestinal motility and secretory processing. However, the principal recognized actions of pancreatic glucagon are to promote hepatic glycogenolysis and glyconeogenesis, resulting in an elevation of blood sugar levels. In this regard, the actions of glucagon are counter regulatory to those of insulin and may contribute to the hyperglycemia that accompanies *Diabetes mellitus* (Lund, P. K., et al., *Proc. Natl. Acad. Sci. U.S.A.,* 79:345–349 (1982)).

When glucagon binds to its receptor on insulin producing cells, cAMP production increases which in turn stimulates insulin expression (Korman, L. Y., et al., *Diabetes,* 34:717–722 (1985)). Moreover, high levels of insulin down-regulate glucagon synthesis by a feedback inhibition mechanism (Ganong, W. F., *Review of Medical Physiology,* Lange Publications, Los Altos, Calif., p. 273 (1979)). Thus, the expression of glucagon is carefully regulated by insulin, and ultimately by serum glucose levels.

Preproglucagon, the zymogen form of glucagon, is translated from a 360 base pair gene and is processed to form proglucagon (Lund, et al., *Proc. Natl. Acad. Sci. U.S.A.* 79:345–349 (1982)). Patzelt, et al. (*Nature,* 282:260–266 (1979)) demonstrated that proglucagon is further processed into glucagon and a second peptide. Later experiments demonstrated that proglucagon is cleaved carboxyl to Lys-Arg or Arg-Arg residues (Lund, P. K., et al., Lopez L. C., et al., *Proc. Natl. Acad. Sci. U.S.A.,* 80:5485–5489 (1983), and Bell, G. I., et al., *Nature* 302:716–718 (1983)). Bell, G. I., et al., also discovered that proglucagon contained three discrete and highly homologous peptide regions which were designated glucagon, glucagon-like peptide 1 (GLP-1), and glucagon-like peptide 2 (GLP-2). Lopez, et al., demonstrated that GLP-1 was a 37 amino acid peptide and that GLP-2 was a 34 amino acid peptide. Analogous studies on the structure of rat preproglucagon revealed a similar pattern of proteolytic cleavage at Lys-Arg or Arg-Arg residues, resulting in the formation of glucagon, GLP-1, and GLP-2 (Heinrich, G., et al., *Endocrinol.,* 115:2176–2181 (1984)). Finally, human, rat, bovine, and hamster sequences of GLP-1 have been found to be identical (Ghiglione, M., et al., *Diabetologia,* 27:599–600 (1984)).

The conclusion reached by Lopez, et al., regarding the size of GLP-1 was confirmed by studying the molecular forms of GLP-1 found in the human pancreas (Uttenthal, L. O., et al. *J. Clin. Endocrinol. Metabol.,* 61:472–479 (1985)). Their research showed that GLP-1 and GLP-2 are present in the pancreas as 37 and 34 amino acid peptides respectively.

The similarity between GLP-1 and glucagon suggested to early investigators that GLP-1 might have biological activity. Although some investigators found that GLP-1 could induce rat brain cells to synthesize cAMP (Hoosein, N. M., et al., *Febs Lett.* 178:83–86 (1984)), other investigators failed to identify any physiological role for GLP-1 (Lopez, L. C., et al. supra). However, GLP-1 is now known to stimulate insulin secretion (insulinotropic action) causing glucose uptake by cells which decreases serum glucose levels (see, e.g., Mojsov, S., *Int. J. Peptide Protein Research,* 40:333–343 (1992)).

Numerous GLP-1 analogs demonstrating insulinotropic action are known in the art. These variants and analogs include, for example, GLP-1(7–36), Gln$^9$-GLP-1(7–37), D-Gln$^9$-GLP-1(7–37), acetyl-Lys$^9$-GLP-1(7–37), Thr$^{16}$-Lys$^{18}$-GLP-1(7–37), and Lys$^{18}$-GLP-1(7–37). Derivatives of GLP-1 include, for example, acid addition salts, carboxylate salts, lower alkyl esters, and amides (see, e.g., WO91/11457 (1991)). More importantly, it was demonstrated using GLP-1(8–37)OH that the histidine residue at position 7 is very important to insulinotropic activity of GLP-1 (Suzuki, S., et al. *Diabetes Res.; Clinical Practice* 5 (Supp. 1):S30 (1988).

In view of the above, it was most surprising when the present inventors discovered that administering N-terminal deletion mutants of GLP-1 to experimental animals caused an increase in serum glucose uptake in the absence of any insulinotropic activity. This discovery suggests that an entirely new mechanism for lowering elevated blood glucose levels may exist and directly lead to the present invention.

Accordingly, the primary object of this invention is to provide novel, C-terminal GLP-1 fragments having no insulinotropic action but which are nonetheless useful for treating diabetes and hyperglycemic conditions. Further objects of the present invention are pharmaceutical compositions that contain biologically-active GLP-1 fragments, as well as methods for using such compounds to treat diabetes.

SUMMARY OF THE INVENTION

The present invention provides biologically-active GLP-1 fragments of the formula:

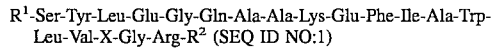
R$^1$-Ser-Tyr-Leu-Glu-Gly-Gln-Ala-Ala-Lys-Glu-Phe-Ile-Ala-Trp-Leu-Val-X-Gly-Arg-R$^2$ (SEQ ID NO:1)

wherein R$^1$ is selected from the group consisting of:
a) H$_2$N;
b) H$_2$N-Ser;
c) H$_2$N-Val-Ser;
d) H$_2$N-Asp-Val-Ser;
e) H$_2$N-Ser-Asp-Val-Ser (SEQ ID NO:2);
f) H$_2$N-Thr-Ser-Asp-Val-Ser (SEQ ID NO: 3);
g) H$_2$N-Phe-Thr-Ser-Asp-Val-Ser (SEQ ID NO: 4);
h) H$_2$N-Thr-Phe-Thr-Ser-Asp-Val-Ser (SEQ ID NO:5);
i) H$_2$N-Gly-Thr-Phe-Thr-Ser-Asp-Val-Ser (SEQ ID NO: 6);

j) H₂N-Glu-Gly-Thr-Phe-Thr-Ser-Asp-Val-Ser (SEQ ID NO: 7); or, k) H₂N-Ala-Glu-Gly-Thr-Phe-Thr-Ser-Asp-Val-Ser (SEQ ID NO: 8);

X is selected from the group consisting of Lys or Arg; and wherein R² is selected from the group consisting of NH₂, OH, Gly-NH₂, or Gly-OH.

The invention further provides pharmaceutical compositions comprising the claimed GLP-1 fragments and methods for treating diabetes or hyperglycemia in a mammal comprising administering the GLP-1 fragments or compositions to the mammal.

DETAILED DESCRIPTION OF THE INVENTION

In one embodiment, the present invention provides novel, biologically-active, C-terminal fragments of GLP-1. For purposes of this specification, the term "biologically-active" refers to the ability of a substance to lower elevated levels of blood glucose in a mammal without stimulating insulin secretion.

The GLP-1 fragments of the present invention range from 19 to 29 amino acid residues in length. Eleven different R¹ groups are consistent with the invention. Within the R¹ group, there is a individual, incremental rank order of preference that corresponds to chain length. Specifically, k) is the most preferred group, and a) is the least preferred group. Within the X group Lys is preferred, and within the R² group, Gly-OH is preferred, and NH₂ is more preferred.

Given the sequence information herein disclosed and the state of the art in solid phase protein synthesis, biologically-active GLP-1 fragments can be obtained via chemical synthesis. However, it also is possible to obtain a biologically-active GLP-1 fragment by fragmenting proglucagon using, for example, proteolytic enzymes. Moreover, recombinant DNA techniques may be used to express biologically-active GLP-1 fragments.

The principles of solid phase chemical synthesis of polypeptides are well known in the art and may be found in general texts in the area such as Dugas, H. and Penney, C., *Bioorganic Chemistry* (1981) Springer-Verlag, New York, pgs. 54–92, Merrifield, J. M., Chem. Soc., 85:2149 (1962), and Stewart and Young, *Solid Phase Peptide Synthesis*, pp. 24–66, Freeman (San Francisco, 1969).

For example, a biologically-active GLP-1 fragment may be synthesized by solid-phase methodology utilizing an Applied Biosystems 430A peptide synthesizer (Applied Biosystems, Inc., 850 Lincoln Center Drive, Foster City, Calif. 94404) and synthesis cycles supplied by Applied Biosystems. Boc amino acids and other reagents are commercially available from Applied Biosystems and other chemical supply houses. Sequential Boc chemistry using double couple protocols are applied to the starting p-methyl benzhydryl amine resins for the production of C-terminal carboxamides. For the production of C-terminal acids, the corresponding PAM resin is used. Asp, Gln, and Arg are coupled using preformed hydroxy benzotriazole esters. The following side chain protecting groups may be used:

Arg, Tosyl
Asp, cyclohexyl
Glu, cyclohexyl
Ser, Benzyl
Thr, Benzyl
Tyr, 4-bromo carbobenzoxy Boc deprotection may be accomplished with trifluoroacetic acid in methylene chloride. Following completion of the synthesis the peptides may be deprotected and cleaved from the resin with anhydrous hydrogen fluoride (HF) containing 10% meta-cresol. Cleavage of the side chain protecting group(s) and of the peptide from the resin is carried out at zero degrees centigrade or below, preferably −20° C. for thirty minutes followed by thirty minutes at 0° C. After removal of the HF, the peptide/resin is washed with ether, and the peptide extracted with glacial acetic acid and lyophilized.

The preparation of protected, unprotected, and partially protected GLP-1 has been described in the art. See U.S. Pat. Nos. 5,120,712 and 5,118,666, herein incorporated by reference, and Orskov, C., et al., *J. Biol. Chem.*, 264 (22):12826–12829 (1989) and WO 91/11457 (Buckley, D. I., et al., published Aug. 8, 1991).

Likewise, the state of the art in molecular biology provides the ordinarily skilled artisan another means by which biologically-active GLP-1 fragments can be obtained. Although GLP-1 fragments may be produced by solid phase peptide synthesis, recombinant methods, or by fragmenting glucagon, recombinant methods may be preferable because higher yields are possible. The basic steps in the recombinant production of a biologically-active GLP-1 fragment are:

a) isolating a natural DNA sequence encoding GLP-1 or constructing a synthetic or semi-synthetic DNA coding sequence for GLP-1, b) placing the coding sequence into an expression vector in a manner suitable for expressing proteins either alone or as a fusion proteins, c) transforming an appropriate eukaryotic or prokaryotic host cell with the expression vector, d) culturing the transformed host cell under conditions that will permit expression of a GLP-1 intermediate, and e) recovering and purifying the recombinantly produced protein.

As previously stated, the coding sequences for GLP-1 fragments may be wholly synthetic or the result of modifications to the larger, native glucagon-encoding DNA. A DNA sequence that encodes preproglucagon is presented in Lund, et al., *Proc. Natl. Acad. Sci. U.S.A.* 79:345–349 (1982) and may be used as starting material in the recombinant production of a biologically-active GLP-1 fragment by altering the native sequence to achieve the desired results.

Synthetic genes, the in vitro or in vivo transcription and translation of which results in the production of a biologically-active GLP-1 fragment, may be constructed by techniques well known in the art. Owing to the natural degeneracy of the genetic code, the skilled artisan will recognize that a sizable yet definite number of DNA sequences may be constructed which encode GLP-1 intermediates.

The methodology of synthetic gene construction is well known in the art. See Brown, et al. (1979) *Methods in Enzymology*, Academic Press, N.Y., Vol. 68, pgs. 109–151. DNA sequences that encode GLP-1 intermediates can be designed based on the amino acid sequences herein disclosed. Once designed, the sequence itself may be generated using conventional DNA synthesizing apparatus such as the Applied Biosystems Model 380A or 380B DNA synthesizers (Applied Biosystems, Inc., 850 Lincoln Center Drive, Foster City, Calif. 94404).

To effect the expression of a biologically-active GPL-1 fragment, one inserts the engineered synthetic DNA sequence in any one of many appropriate recombinant DNA expression vectors through the use of appropriate restriction endonucleases. See generally Maniatis et al. (1989) *Molecular Cloning; A Laboratory Manual*, Cold Springs Harbor Laboratory Press, N.Y., Vol. 1–3. Restriction endonuclease cleavage sites are engineered into either end of the DNA encoding the GLP-1 fragment to facilitate isolation from, and integration into, known amplification and expression vectors. The particular endonucleases employed will be dictated by the restriction endonuclease cleavage pattern of the parent expression vector to be employed. The choice of restriction sites are chosen so as to properly orient the coding sequence with control sequences to achieve proper in-frame reading and expression of the protein of interest. The coding sequence must be positioned so as to be in proper reading frame with the promoter and ribosome binding site of the expression vector, both of which are functional in the host cell in which the protein is to be expressed.

To achieve efficient transcription of the coding region, it must be operably associated with a promoter-operator region. Therefore, the promoter-operator region of the gene is placed in the same sequential orientation with respect to the ATG start codon of the coding region.

A variety of expression vectors useful for transforming prokaryotic and eukaryotic cells are well known in the art. See *The Promega Biological Research Products Catalogue* (1992) (Promega Corp., 2800 Woods Hollow Road, Madison, Wis., 53711–5399); and *The Stratagene Cloning Systems Catalogue* (1992) (Stratagene Corp., 11011 North Torrey Pines Road, La Jolla, Calif., 92037). Also, U.S. Pat. No. 4,710,473 describes circular DNA plasmid transformation vectors useful for expression of exogenous genes in *E. coli* at high levels. These plasmids are useful as transformation vectors in recombinant DNA procedures and:
(a) confer on the plasmid the capacity for autonomous replication in a host cell;
(b) control autonomous plasmid replication in relation to the temperature at which host cell cultures are maintained;
(c) stabilize maintenance of the plasmid in host cell populations;
(d) direct synthesis of a protein prod. indicative of plasmid maintenance in a host cell population;
(e) provide in series restriction endonuclease recognition sites unique to the plasmid; and
(f) terminate mRNA transcription.

These circular DNA plasmids are useful as vectors in recombinant DNA procedures for securing high levels of expression of exogenous genes.

Having constructed an expression vector for a biologically-active GLP-1 fragment, the next step is to place the vector into a suitable cell and thereby construct a recombinant host cell useful for expressing a biologically-active GLP-1 fragment. Techniques for transforming cells with recombinant DNA vectors are well known in the art and may be found in such general references as Maniatis, et al. supra. Host cells made be constructed from either eukaryotic or prokaryotic cells. Eukaryotic host cells are capable of carrying out post-translational glycosylations on expressed proteins and some are capable of secreting the desired protein into the culture medium.

Prokaryotic host cells generally produce the protein at higher rates, are easier to culture but are not capable of glycosylating the final protein. Proteins which are expressed in high-level bacterial expression systems may aggregate in granules or inclusion bodies which contain high levels of the overexpressed protein. Such protein aggregates must be solubilized, denatured and refolded using techniques well known in the art. See Kreuger, et al. (1990) in *Protein Folding*, Gierasch and King, eds., pgs 136–142, American Association for the Advancement of Science Publication No. 89-18S, Washington, D.C.; and U.S. Pat. No. 4,923,967.

Regardless of the methods used to produce a biologically-active GLP-1 fragment, purification of the protein generally will be required. Methods for purifying proteins are well known in the art and include conventional chromatography, including ion and cation exchange, hydrophobic interaction, and immuno-affinity chromatographic media. The amino acid sequences here in disclosed in conjunction with well known protein purification methods will enable the ordinarily skilled artisan to purify biologically-active GLP-1 fragments claimed herein.

The present invention also includes salt forms of biologically-active GLP-1 fragments. A biologically-active GLP-1 fragment of the invention may be sufficiently acidic or sufficiently basic to react with any of a number of inorganic bases, and inorganic and organic acids, to form a salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylienesulfonate, phenylacetate, phenylpropionate, phenylbutyrate, citrate, lactate, gammahydroxybutyrate, glycolate, tartrate, methanesulfonate, propanesulfonate, naphthalene-1-sulfonate, naphthalene-2-sulfonate, mandelate, and the like. Preferred acid addition salts are those formed width mineral acids such as hydrochloric acid and hydrobromic acid, and, especially, hydrochloric acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like. Salt forms of GLP-1 analogs are particularly preferred. Of course, when the compounds of this invention are used for therapeutic purposes, those compounds may also be in the form of a salt, but the salt must be pharmaceutically acceptable.

The inability of a GLP-1 fragment to stimulate insulin secretion may be determined by providing a GLP-1 fragment to cultured animal cells, such as the RIN-38 rat insulinoma cell line, and monitoring the release of immunoreactive insulin (IRI) into the media. Alternatively one can inject a GLP-1 fragment into an animal and monitor plasma levels of immunoreactive insulin (IRI).

The presence of IRI is detected through the use of a radioimmunoassay which can specifically detect insulin. Any radioimmunoassay capable of detecting the presence of IRI may be employed; one such assay is a modification of the method of Albano, J. D. M., et al., *Acta Endocrinol.*, 70:487–509 (1972). In this modification, a phosphate/albumin buffer with a pH of 7.4 is employed. The incubation is prepared with the consecutive addition of 500 µl of phosphate buffer, 50 µl of perfusate sample or rat insulin standard in perfusate, 100 µl of anti-insulin antiserum (Wellcome Laboratories; 1:40,000 dilution), and 100 µl of [$^{125}$I] insulin, giving a total volume of 750 μl in a 10×75 mm disposable glass tube. After incubation for 2–3 days at 4° C., free insulin is separated from antibody-bound insulin by charcoal separation. The assay sensitivity is 1–2 uU/mL. In order to measure the release of IRI into the cell culture medium of cells grown in tissue culture, one preferably incorporates radioactive label into proinsulin. Although any radioactive label capable of labeling a polypeptide can be used, it is preferable to use $^3$H leucine in order to obtain labeled proinsulin.

To determine whether a GLP-1 fragment has insulinotropic properties may also be determined by pancreatic infusion. The in situ isolated perfused rat pancreas assay is a modification of the method of Penhos, J. C., et al., *Diabetes*, 18:733–738 (1969). Fasted male Charles River strain albino rats, weighing 350–600 g, are anesthetized with an intraperitoneal injection of Amytal Sodium (Eli Lilly and Co.: 160 ng/kg). Renal, adrenal, gastric, and lower colonic blood vessels are ligated. The entire intestine is resected except for about four cm of duodenum and the descending colon and rectum. Therefore, only a small part of the intestine is perfused, minimizing possible interference by enteric substances with glucagon-like immunoreactivity. The perfusate is a modified Krebs-Ringer bicarbonate buffer with 4% dextran T70 and 0.2% bovine serum albumin (fraction V, and is bubbled with 95% $O_2$ and 5% $CO_2$. A nonpulsatile flow, 4-channel roller bearing pump (Buchler polystatic, Buchler Instruments Division, Nuclear-Chicago Corp.) is used, and a switch from one perfusate source to another is accomplished by switching a 3-way stopcock. The manner in which perfusion is performed, monitored, and analyzed follow the method of Weir, G. C., et al., *J. Clin. Inestigat.* 54:1403–1412 (1974), which is hereby incorporated by reference.

The present invention also provides pharmaceutical compositions comprising a GLP-1 fragment of the present invention in combination with a pharmaceutically acceptable carrier, diluent, or excipient. Such pharmaceutical compositions are prepared in a manner well known in the pharmaceutical art, and are administered individually or in combination with other therapeutic agents, preferably via parenteral routes. Especially preferred routes include intramuscular and subcutaneous administration.

Parenteral daily dosages, preferably a single, daily dose, are in the range from about 1 pg/kg to about 1,000 μg/kg of body weight, although lower or higher dosages may be administered. The required dosage will depend upon the severity of the condition of the patient and upon such criteria as the patient's height, weight, sex, age, and medical history.

In making the compositions of the present invention, the active ingredient, which comprises at least one protein of the present invention, is usually mixed with an excipient or diluted by an excipient. When an excipient is used as a diluent, it may be a solid, semi-solid, or liquid material which acts as a vehicle, carrier, or medium for the active ingredient.

In preparing a formulation, it may be necessary to mill the active compound to provide the appropriate particle size prior to combining with the other ingredients. If the active protein is substantially insoluble, it ordinarily is milled to particle size of less than about 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, trehalose, sorbitol, mannitol, starches, gum acacia, calcium silicate, microcrystalline cellulose, polyvinylpyrrolidone, cellulose, water, syrup, and methyl cellulose. The formulations can additionally include lubricating agents such as talc, magnesium stearate and mineral oil, wetting agents, emulsifying and suspending agents, preserving agents such as methyl- and propylhydroxybenzoates, sweetening agents or flavoring agents. The compositions of the invention can be formulated so as to provide quick, sustained or delayed release of the active ingredient after administration to the patient by employing procedures well known in the art.

The compositions are preferably formulated in a unit dosage form with each dosage normally containing from about 50 μg to about 100 mg, more usually from about 1 mg to about 10 mg of the active ingredient. The term "unit dosage form" refers to physically discrete units suitable as unitary dosages for human subjects and other mammals, each unit containing a predetermined quantity of active material calculated to produce the desired therapeutic effect in association with a suitable pharmaceutical excipient.

For the purpose of parenteral administration, compositions containing a protein of the present invention preferably are combined with distilled water and the pH is adjusted to about 6.0 to about 9.0.

Additional pharmaceutical methods may be employed to control the duration of action. Controlled release preparations may be achieved by the use of polymers to complex or absorb a compound of the present invention. The controlled delivery may be exercised by selecting appropriate macromolecules (for example, polyesters, polyamino acids, polyvinylpyrrolidone, ethylenevinyl acetate, methylcellulose, carboxymethylcellulose, and protamine sulfate) and the concentration of macromolecules as well as the methods of incorporation in order to control release.

Another possible method to control the duration of action by controlled release preparations is to incorporate a protein of the present invention into particles of a polymeric material such as polyesters, polyamino acids, hydrogels, poly lactic acid) or ethylene vinylacetate copolymers.

Alternatively, instead of incorporating a compound into these polymeric particles, it is possible to entrap a compound of the present invention in microcapsules prepared, for example, by coacervation techniques or by interfacial polymerization, for example, hydroxymethylcellulose or gelatin-microcapsules, respectively, or in colloidal drug delivery systems, for example, liposomes, albumin microspheres, microemulsions, nanoparticles, and nanocapsules, or in macroemulsions. Such teachings are disclosed in *Remington's Pharmaceutical Sciences* (1980).

Similarly, the present invention provides a method for treating diabetes or hyperglycemia in a mammal, preferably a human, in need of such treatment comprising administering an effective amount of a GLP-1 fragment or composition of the present invention, to such a mammal.

By way of illustration, the following examples are provided to help describe how to make and practice the various embodiments of the invention. These example are in no way meant to limit the scope of the invention.

EXAMPLE 1

Synthesis of GLP-1(9–36)NH$_2$

GLP-1(9–36)NH$_2$ (SEQ ID NO:9) was produced by solid phase peptide chemistry on an Applied Biosystems (ABI) 460A peptide synthesizer using a MBHA resin (Applied Biosystems Inc., lot #A1A023, 0.77 mol/g). All amino acids had their α-amino groups protected by the tert-butyloxycarbonyl (t-Boc) group. Those with reactive side chains had them protected as follows: Arg(Tos); Lys(Cl-Z); Trp(CHO); Glu(CHex); Tyr(Br-Z); Ser(Bzl); Asp(OBzl); Thr(Bzl).

The protected amino acids were activated in dichloromethane (DCM) with one half an equivalent of dicyclohexylcarbodiimide (DCC) per equivalent of amino acid to give the symmetric anhydride of the amino acid. However, arginine, glutamine, and glycine residues were activated by forming the 1-hydroxybenzotriazole (HOBt) esters of these amino acids (1:1:1 equivalents of amino acid, HOBt, and DCC in dimtethylformamide (DMF)).

Residues were sequentially connected from the C-terminal towards the N-terminal end with a series of coupling and deprotection cycles. A coupling cycle consisted of the activated amino acid undergoing nucleophilic substitution by the free primary amine of the previously coupled amino acid. Deprotection was the removal of the N-terminal blocking group Boc with anhydrous trifluoroacetic acid (TFA). This generated a free amine group after neutralization with diisopropylethylamine (DIEA).

The synthesis scale was 0.5 mmol. The concentration of functional sites on the MBHA-resin was 0.77 mmol/g; 649 mg of resin was used. A two fold molar excess of the symmetric anhydride was used for all of the amino acids. The C-terminal Arginine was coupled to the MBHA-resin via standard protocols. All residues were double-coupled. That is each residue was coupled to the resin twice. The second coupling was performed without a Boc deprotection step prior to re-addition of the amino acid. This helped to completely react all of the free amine groups on the resin. The tryptophan residue was quadruple coupled.

After the second coupling step of each double-coupling cycle the N-terminal Boc groups were removed with anhydrous TFA and neutralized with DIEA.

The formyl side chain blocking group on the tryptophan residue was removed with piperidine in DMF prior to cleaving the peptide from the resin. After the peptidyl-resin was transferred to a 50 ml sintered glass funnel, it washed several times with DCM and DMF. Then 3–5 ml of a 50/50 piperidine/DMF solution was added to the peptide-resin so that it was just covered. After 5 minuets the piperidine/DMF was removed by vacuum and 3–5 ml of piperidine/DMF was added. After 10 minutes, the piperidine/DMF again was removed by vacuum filtration and 15–20 ml of piperidine/DMF was added. After 15 minutes the piperidine/DMF was removed and the peptidyl-resin washed with DMF several times followed by DCM. The peptidyl-resin was then placed into a vacuum oven (no heat) to complete solvent removal.

Once the amino acids were sequentially coupled, and the formyl group removed, the peptide was liberated from the resin by hydrolysis with liquid hydrofluoric acid (HF) at 0° C. for one hour using a Teflon reaction vessel. In the process of liberating the peptide, the C terminal hydroxide was displaced with an amide group from the MBHA-resin (see Matseuda and Stewart, *Peptides* 2:45 (1981)). For every gram of peptidyl-resin, 1 ml of m-cresol scavenger was added and 10 ml of liquid HF used. The scavenger prevented the reattachment of side chain blocking groups (released as carbocations) to the peptide. After one hour, the HF was removed by vacuum leaving a slurry of peptide, resin, and m-cresol.

The peptide was then precipitated in the HF reaction vessel with ice cold diethyl ether. The precipitate was transferred to a 150 ml sintered glass funnel along with several ether rinses. The peptide/resin physical mixture was washed several times with cold ether to remove residual HF and m-cresol. The second step was to extract the peptide away from the resin using 10% acetic acid in water (v/v). Vacuum filtration into a clean round bottom flask yielded a crude peptide solution.

EXAMPLE 2

Purification

The crude peptide solution obtained in Example 1 was run on reverse-phase analytical HPLC at pH 2.3. The chromatogram showed a major peak indicating that an appreciable amount of the desired product was formed and that preparative purification was warranted.

The entire crude peptide solution was run on preparative reverse phase HPLC at pH 2 under the following conditions:
Buffers: A=0.1% TFA, 10% acetonitrile
B=0.1% TFA, 50% acetonitrile
Column: Vydac C18 (2.2×25 cm)
Temperature: approximately 20° C.
Detector: 280 nm
Flow: 2.0 ml/min
Gradient: 25% B to 100% B over 1,000 minutes
The title peptide eluted at approximately 34% acetonitrile as identified by analytical HPLC and electrospray mass spectroscopy. The approximate yield was 125 mg of 60% purity by analytical HPLC at pH 2.3.

The approximately 60% pure, 125 mg yield was then run on preparative reverse phase HPLC at pH 7.7 under the following conditions:
Buffers: A=0.1M (NH$_4$)HCO$_3$, 10% acetonitrile
B=A, 50% acetonitrile
Column: Vydac C18 (2.2×25 cm)
Temperature: approximately 20° C.
Detector: 280 nm
Flow: 2.0 ml/min
Gradient: 35% B to 70% B over 1,000 minutes
The title peptide eluted between 32% and 37% acetonitrile as identified by analytical HPLC. The approximate yield was 11%.

EXAMPLE 3

Synthesis and Purification of GLP-1(9–37)OH

GLP-1(9–37)OH (SEQ ID NO:10) was prepared by solid phase synthesis on a Model 430A peptide synthesizer (Applied Biosystems, Foster City, Calif.) using the Boc protecting strategy. The side chain protecting groups were: Asp (Chxl), Glu (OBzl), Ser (Bzl), Thr (Bzl), Lys (Cl-Z), His (BOM), Trp (CHO), Tyr (Br-Z), and Arg (Tos). All except for Asp (Chxl) (Peptides International) were obtained from Applied Biosystems. Each residue was double coupled using either DCC initiated symetric anhydride or HOBT activation. The 30 residue intermediate was left attached to the resin. The title compound was isolated in substantial accordance with Example 2 and was eluted between 33% and 34 % acetonitrile as identified by analytical HPLC. The approximate yield was 11%.

EXAMPLE 4

Synthesis and Purification of GLP-1(8–37)OH

GLP-1(8–37)OH (SEQ ID NO:12) was synthesized in substantial accordance with Example 3 and isolated according to Example 2. The title compound eluted at approximately 42% acetonitrile as identified by analytical HPLC. The approximate yield was 13%.

EXAMPLE 5

Synthesis and Purification of GLP-1(R26)(9-36)NH$_2$

GLP-1(R26)(9-36)NH$_2$ (SEQ ID NO:13) was synthesized in substantial accordance with Example 1 and isolated according to Example 2. The title compound eluted at approximately 34% acetonitrile as identified by analytical HPLC. The approximate yield was 4.1%.

EXAMPLE 6

In vivo Hyperglycemic Clamp Assay (Glucose Up-take Assay)

(a) Animal Preparation:

Male Sprague-Dawley rats (Charles Rivers) weighing about 350 grams were allowed to acclimate to their surroundings for a week after which they were cannulated under isoflurane inhalation anesthetic. Two catheters were implanted into the jugular vein for infusions of glucose and GLP-1 fragment. Another catheter was implanted into the carotid artery for sampling blood. The catheters were exteriorized through the skin at the vertex of the head, filled with a glycerol/heparin solution (30 ml glycerol/10 ml heparin from a 1000 u/ml stock solution), and closed off with a one centimeter stainless steel plug. The rats were housed individually in wire mesh cages and were fed ad libitum on a standard rat chow diet. Each animal was given at least one week to recover from surgery before testing any GLP-1 fragments for biological activity.

(b) Assay

The rats were fasted overnight; on the morning of the experiment, sampling tubes were connected to the indwelling catheters, and the tubes were enclosed in a light weight stainless steel spring for protection. The rats were acclimated to their cages for 15 minutes. All experiments were carried out in conscious, free moving rats.

A basal blood sample was taken for measurement of insulin and glucose levels at time zero on the timer. The rats were then given a bolus of 20% dextrose to raise plasma glucose to either 150 mg/dl (8.3 mM) or 200 mg/dl (11.2 mM). Plasma glucose levels were maintained at the chosen level by measuring plasma glucose levels approximately every 5 minutes and adjusting the calibrated variable infusion pump as needed to maintain the established blood glucose levels. Blood samples were collected at 45 and 60 minutes for the control period measurements. At 60 minutes into the clamp, 0.3 nmol/kg of the experimental GLP-1 fragment was injected via the jugular vein catheter and flushed with saline. Blood samples were taken to measure glucose and insulin at 62, 64, 66, 68, 70, 75, 80, 90 100, 110, and 120 minutes.

The blood samples were centrifuged in a micro centrifuge to separate the plasma component. Plasma glucose was measured on a Beckman Glucose analyzer II using the glucose oxidase method. Plasma insulin was determined by standard radio immunoassay as per the manufacturer's directions (Diagnostic Products Corp.). The activity of the GLP-1 fragment was determined by the percentage change in glucose infusion rate and change in insulin secreted. These two parameters were compared to control rats that received only diluent. Test results are summarized in Tables 1-6.

Note: This assay is based on reports that GLP-1 insulinotropic action is glucose dependent. The assay protocol eliminates variability due to falling glucose levels in other protocols using the "bolus" method. The hyperglycemic clamp involved administration of variable amounts of glucose (20% dextrose) to maintain glucose at a constant level of 8.3 or 11.2 mM in fasted normal Sprague-Dawley rats. The hyperglycemic clamp is maintained for 1 hour after which the GLP-1 fragment is injected as a bolus through the jugular vein. The hyperglycemic clamp is continued for another hour. The glucose infusion rate (GIR) in the last 15 minutes of the control period and after the injection of the peptide is calculated. The activity of the peptide is determined by the increase in glucose infusion rate and change in insulin secreted after the injection of the peptide.

TABLE 1

| (200 mg/dl plasma glucose) | | | | |
|---|---|---|---|---|
| | PBS (diluent; n = 7) | | GLP-1(7-37)OH; n = 4 | |
| Time (min.) | % Change in GIR | Standard Error | % Change in GIR | Standard Error |
| 60 | 25.689 | 2.716 | 20.449 | 4.026 |
| 62 | 4.863 | 1.244 | 25.050 | 3.714 |
| 64 | 25.689 | 2.716 | 23.583 | 3.534 |
| 66 | 10.676 | 5.676 | 15.374 | 10.515 |
| 68 | 8.697 | 2.712 | 19.465 | 11.281 |
| 70 | 10.160 | 2.174 | 50.305 | 19.836 |
| 75 | 13.294 | 2.911 | 71.461 | 16.465 |
| 80 | 14.122 | 2.394 | 88.390 | 11.481 |
| 85 | 17.932 | 3.836 | 86.482 | 11.788 |
| 90 | 19.634 | 4.426 | 55.677 | 18.763 |
| 100 | 14.673 | 4.717 | 11.304 | 14.725 |
| 110 | −3.426 | 8.818 | −12.411 | 16.973 |
| 120 | −10.648 | 8.109 | −7.123 | 2.855 |
| 130 | −13.268 | 6.426 | −17.745 | 5.058 |
| 140 | −15.912 | 5.752 | −15.311 | 5.131 |
| 150 | −17.131 | 5.443 | −21.279 | 8.568 |

TABLE 2

| (200 mg/dl plasma glucose) | | | | |
|---|---|---|---|---|
| | GLP-1 (9-37)OH (n = 4) (SEQ ID NO: 10) | | GLP-1 (9-36)NH$_2$ (n = 7) (SEQ ID NO: 9) | |
| Time (min.) | % Change in GIR | Standard Error | % Change in GIR | Standard Error |
| 60 | 18.229 | 1.388 | 21.936 | 2.233 |
| 62 | 20.833 | 1.533 | −1.287 | 2.037 |
| 64 | 20.045 | 1.403 | -0.635 | 2.334 |
| 66 | 9.789 | 6.041 | 10.697 | 2.488 |
| 68 | 17.016 | 8.986 | 24.584 | 6.058 |
| 70 | 24.101 | 13.680 | 46.387 | 9.893 |
| 75 | 30.211 | 7.544 | 61.185 | 8.717 |
| 80 | 13.304 | 10.839 | 48.254 | 7.200 |
| 85 | −1.974 | 20.769 | 34.689 | 5.518 |
| 90 | −16.488 | 23.585 | 17.272 | 10.998 |
| 100 | −34.401 | 27.049 | 7.537 | 8.776 |
| 110 | −48.313 | 25.980 | −0.920 | 5.874 |
| 120 | −55.055 | 23.790 | 4.716 | 2.813 |
| 130 | −56.835 | 22.146 | 3.818 | 3.368 |
| 140 | −56.835 | 22.146 | −6.783 | 4.944 |
| 150 | −56.835 | 22.146 | 1.333 | 8.147 |

TABLE 3

(200 mg/dl plasma glucose)
GLP-1(Arg-26) (9-36)NH₂; n = 3
(SEQ ID NO: 13)

| Time (min.) | % Change in GIR | Standard Error |
|---|---|---|
| 60 | 19.020 | 2.729 |
| 62 | 2.128 | 0.535 |
| 64 | 3.752 | 1.727 |
| 66 | 11.602 | 7.040 |
| 68 | 29.976 | 10.865 |
| 70 | 37.819 | 10.199 |
| 75 | 50.568 | 4.964 |
| 80 | 42.526 | 15.034 |
| 85 | 16.548 | 29.505 |
| 90 | −6.165 | 29.975 |
| 100 | −18.164 | 15.592 |
| 110 | −35.351 | 15.112 |
| 120 | −48.404 | 22.891 |

TABLE 4

(200 mg/dl plasma glucose)

| | PBS (diluent; n = 6) | | GLP-1(7-37)OH (n = 4) | |
|---|---|---|---|---|
| Time (min.) | Plasma Insulin Change (ng/ml) | Standard Error | Plasma Insulin Change (ng/ml) | Standard Error |
| 60 | 1.787 | 0.231 | 1.887 | 0.303 |
| 62 | −0.189 | 0.145 | 11.101 | 1.259 |
| 64 | −0.313 | 0.179 | 4.219 | 1.099 |
| 66 | −0.242 | 0.257 | 3.246 | 0.998 |
| 68 | −0.529 | 0.168 | 1.359 | 0.751 |
| 70 | −0.090 | 0.237 | −0.208 | 0.535 |
| 75 | −0.114 | 0.245 | −0.692 | 0.343 |
| 80 | −0.188 | 0.227 | −0.456 | 0.228 |
| 85 | −0.068 | 0.289 | −0.177 | 0.179 |
| 90 | −0.044 | 0.253 | −0.250 | 0.438 |
| 100 | 0.104 | 0.410 | −0.301 | 0.500 |
| 110 | −0.084 | 0.348 | −0.222 | 0.989 |
| 120 | 0.169 | 0.350 | −0.405 | 0.329 |
| 130 | −1.035 | 0.311 | −0.590 | 0.447 |
| 140 | −1.144 | 0.248 | −0.289 | 0.220 |
| 150 | −1.263 | 0.140 | −0.280 | 0.304 |

TABLE 5

(200 mg/dl plasma glucose)

| | GLP-1(9-36)NH₂; n = 7 (SEQ ID NO: 9) | | GLP-1 (R26) (9-36)NH₂; n = 2 (SEQ ID NO: 13) | |
|---|---|---|---|---|
| Time (min.) | Plasma Insulin Change (ng/ml) | Standard Error | Plasma Insulin Change (ng/ml) | Standard Error |
| 60 | 2.429 | 0.362 | 1.692 | 0.206 |
| 62 | −0.521 | 0.234 | 0.693 | 0.992 |
| 64 | −0.765 | 0.223 | 0.025 | 0.146 |
| 66 | −0.637 | 0.192 | 0.204 | 0.745 |
| 68 | −0.662 | 0.157 | 0.063 | 0.751 |
| 70 | −0.274 | 0.192 | 0.185 | 0.389 |
| 75 | 0.138 | 0.523 | −0.125 | 0.595 |
| 80 | −0.390 | 0.419 | 0.134 | 0.135 |
| 85 | 0.064 | 0.496 | −0.550 | 0.373 |
| 90 | −0.361 | 0.348 | −0.336 | 0.344 |
| 100 | −0.743 | 0.360 | 0.027 | 0.397 |
| 110 | −0.824 | 0.306 | −0.100 | 0.100 |
| 120 | −0.880 | 0.318 | 0.399 | 0.393 |
| 130 | −0.653 | 0.364 | | |
| 140 | −0.927 | 0.229 | | |
| 150 | −0.450 | 0.435 | | |

TABLE 6

(150 mg/dl plasma glucose)

| | PBS (diluent; n = 4) | | GLP-1(7-37)OH; n = 5 | |
|---|---|---|---|---|
| Time (min.) | % Change in GIR | Standard Error | % Change in GIR | Standard Error |
| 60 | 9.64 | 0.89 | 11.15 | 1.50 |
| 62 | 2.61 | 2.69 | −0.20 | 3.08 |
| 64 | 9.74 | 0.89 | 11.15 | 1.50 |
| 66 | 8.98 | 4.57 | 1.66 | 9.13 |
| 68 | 9.97 | 3.98 | 5.64 | 13.29 |
| 70 | 8.69 | 4.46 | 19.95 | 11.02 |
| 75 | 13.08 | 6.00 | 71.90 | 20.17 |
| 80 | 11.88 | 6.07 | 92.63 | 22.24 |
| 85 | 7.49 | 6.37 | 61.76 | 15.73 |
| 90 | 4.66 | 5.70 | 14.74 | 13.76 |
| 100 | −6.26 | 6.00 | −26.22 | 15.29 |
| 110 | −8.82 | 7.04 | −38.57 | 11.25 |
| 120 | 8.94 | 6.87 | −48.67 | 9.46 |
| 130 | −12.39 | 9.28 | −54.82 | 11.72 |
| 140 | −11.69 | 9.48 | −58.43 | 12.19 |
| 150 | −12.63 | 8.91 | −63.58 | 10.80 |

TABLE 7

(150 mg/dl plasma glucose)
GLP-1(8-37)OH; n = 1
(SEQ ID NO: 12)

| Time (min.) | % Change in GIR |
|---|---|
| 60 | 5.50 |
| 62 | −0.21 |
| 64 | −0.21 |
| 66 | −0.21 |
| 68 | 42.55 |
| 70 | 45.77 |
| 75 | −6.20 |
| 80 | −100.0 |
| 85 | −100.0 |
| 90 | −100.0 |
| 100 | −100.0 |
| 110 | −100.0 |
| 120 | −100.0 |
| 130 | −100.0 |
| 140 | −100.0 |
| 150 | −100.0 |

TABLE 8

(150 mg/dl plasma glucose)

| | PBS (diluent; n = 4) | | GLP-1(7-37)OH (n = 5) | |
|---|---|---|---|---|
| Time (min.) | Plasma Insulin Change (ng/ml) | Standard Error | Plasma Insulin Change (ng/ml) | Standard Error |
| 60 | 0.837 | 0.149 | 1.140 | 0.291 |
| 62 | −0.171 | 0.264 | 7.233 | 0.787 |
| 64 | 0.204 | 0.209 | 1.464 | 0.282 |
| 66 | −0.061 | 0.219 | 0.324 | 0.369 |
| 68 | 0.050 | 0.125 | −0.016 | 0.319 |
| 70 | −0.147 | 0.159 | −0.375 | 0.286 |
| 75 | 0.082 | 0.149 | −0.465 | 0.306 |
| 80 | 0.217 | 0.268 | −0.357 | 0.324 |
| 85 | 0.168 | 0.348 | −0.020 | 0.222 |
| 90 | 0.257 | 0.262 | −0.181 | 0.252 |
| 100 | 0.237 | 0.200 | −0.358 | 0.232 |
| 110 | 0.253 | 0.617 | −0.174 | 0.216 |
| 120 | 0.178 | 0.279 | −0.326 | 0.261 |
| 130 | −0.181 | 0.237 | −0.578 | 0.284 |
| 140 | 0.020 | 0.351 | −0.367 | 0.392 |
| 150 | −0.241 | 0.272 | −0.465 | 0.208 |

TABLE 9

(150 mg/dl plasma glucose)
GLP-1(8-37)OH; n = 1
(SEQ ID NO: 12)

| Time (min.) | Plasma Insulin Change (ng/ml) |
|---|---|
| 60 | 0.792 |
| 62 | -0.213 |
| 64 | -0.079 |
| 66 | -0.026 |
| 68 | 0.655 |
| 70 | 0.324 |
| 75 | -0.412 |
| 80 | -0.217 |
| 85 | -0.489 |
| 90 | -0.163 |
| 100 | -0.334 |
| 110 | -0.324 |
| 120 | -0.792 |
| 130 | -0.792 |
| 140 | -0.792 |
| 150 | -0.792 |

EXAMPLE 7

In vitro GLP-1 Agonist cAMP Assay a) Rat, GLP-1 receptor, membrane preparation:

The published DNA sequence for the rat GLP-1 receptor (Thorens B., et. al. *Proc. Natl. Acad. Sci. U.S.A.* 89:8641–8645 (1992) and the dihydrofolate reductase resistance marker gene were used in conjunction with Polymerase Chain Reaction (PCR) techniques to construct an expression vector. The dihydrofolate reductase-deficient mutant Chinese hamster ovary cell line (DXB-11) was transformed with the vector resulting in a recombinant Chinese hamster ovary cell line that expressed the rat GLP-1 membrane receptor.

Cells were grown to confluency in 10% dialyzed fetal bovine serum/high glucose Dulbecco's Modified Eagle Medium with 0.1% proline at 37° C. The cell were then harvested, and membranes were prepared by first washing the cells with phosphate buffered saline (PBS), then twice with cold buffer (25 mM 4-(2-hydroxyethyl)-1 piperazineethanesulfonic acid (HEPES), 2 mM $MgCl_2$, 1 mM ethylenedinitrilo-tetraacetic acid (EDTA), 20 µg/ml Leupeptin, 1 mM phenylmethyl sulfonyl fluoride (PMSF), 2 µg/ml Aprotinin, 50 µg/ml Trypsin Inhibitor, pH 8.0). The washed cells were resuspended in cold buffer, lysed in a glass Teflon homogenizer and then centrifuged at 35,300 g for 30 minutes at 4° C. The supernatant was removed and the pellet resuspended in cold buffer and homogenized. Two hundred µl aliquots (3.2 mg/ml) were stored at -80° C.

b) Cyclic AMP (cAMP) Assay:

Briefly, 10 µl of membrane prep (80 µg/ml) was preincubated with 10 µl of test compound or reference compound in buffer (25 mM HEPES, 0.2% (w/v) bovine serum albumin (BSA), pH 7.6) at 32° C. for 10 minutes. Five µl of reaction buffer (25 mM HEPES, 0.2% (w/v) BSA, 13 mM $(CH_3COO)_2Mg.4H_2O$, 4 mM adenosine-5'-triphosphate (ATP), 40 nM guanosine 5'-O-3'thiotriphosphate (GTP-∂-s), 25 mM creatine phosphate, creatine kinase 250 U/ml, 1 mM 3-Isobutyl-1-methyl xanthine (IBMX), pH 7.6) was added and incubated for an additional 30 minutes. Incubations were stopped by adding 25 µl 10 mM EDTA and fluorescent tracer (cAMP-β phycoerythrin conjugate). After the incubation was stopped, 25 µl of affinity purified anti-cAMP rabbit antiserum (12.5 ml of 25 mM HEPES, 0.2% (w/v) BSA, pH 7.6 was added to one vial of lyophilized antiserum (Sigma Immuno Chemicals Product No. A-0670). After incubation at room temperature for 45 minutes, 25 µl of anti-rabbit IgG coated assay particles (0.2 % w/v) were added and incubated for an additional 15 minutes. Plates were then evacuated and fluorescence read on a Pandex Screen Machine.

This assay, a particle concentration fluorescence immunoassay, was based on the competition between unlabelled cAMP and a fixed amount of fluorescent labelled cAMP for a limited number of binding sites on a cAMP specific antibody. By keeping the quantity of fluorescent ligand and antibody fixed, the amount of fluorescent ligand bound by the antibody was inversely proportional to the concentration of unlabelled cAMP. The antibody-bound cAMP was then captured by anti-rabbit IgG coated assay particles. Separation of the bound antibody fraction was achieved by filtration on Fluoricon®-Ca Assay Plates. After measuring the fluorescence in the pellet, the amount of bound fluorescent cAMP was calculated. The rate of cAMP production (pmol/min/mg) was then determined by interpolation from a standard curve.

In this assay, agents that demonstrated in vivo insulinotropic action such as GLP-1(7-37)OH showed increasing fluorescent intensity due to increased cAMP concentration. Conversely, agents having no in vivo insulinotropic action failed to stimulate production of cAMP and therefore showed no increase in fluorescent intensity.

TABLE 10

| Dose (nM) | cAMP produced (pmol/min/mg) GLP-1(7-37)OH | cAMP produced (pmol/min/mg) GLP-1(9-36)$NH_2$ |
|---|---|---|
| 0.005 | 25.481 | 21.165 |
| 0.01 | 28.494 | 21.743 |
| 0.02 | 30.453 | 20.678 |
| 0.05 | 30.453 | 22.602 |
| 0.1 | 42.567 | 22.033 |
| 0.4 | 59.037 | 21.460 |
| 1 | 68.697 | 21.588 |
| 4 | 70.282 | 21.046 |
| 10 | 67.494 | 22.320 |
| 100 | 65.665 | 19.156 |

We claim:

1. A GLP-1 fragment of the formula:

R¹-Ser-Tyr-Leu-Glu-Gly-Gln-Ala-Ala-Lys-Glu-Phe-Ile-Ala-TrP-Leu-Val-X-Gly-Arg-R² (SEQ ID NO:1)

wherein R¹ is selected from the group consisting of:
a) H₂N-Glu-Gly-Thr-Phe-Thr-Ser-Asp-Val-Ser (SEQ ID NO:7); and,
b) H₂N-Ala-Glu-Gly-Thr-Phe-Thr-Ser-Asp-Val-Ser (SEQ ID NO:8);

X is selected from the group consisting of Lys and Arg; and wherein R² is selected from the group consisting of NH₂, OH, Gly-NH₂, and Gly-OH, with the proviso that when R¹ is b) and R² is Gly-NH₂ or Gly-OH, X must be Arg.

2. The GLP-1 fragment of claim 1 that has the amino acid sequence:

H₂N-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-NH₂ (SEQ ID NO:9).

3. A pharmaceutical composition comprising the GLP-1 fragment of claim 2 in combination with a pharmaceutically acceptable carrier, diluent, or excipient.

4. A method of treating diabetes in a mammal comprising administering to a mammal in need of such treatment an effective amount of the GLP-1 fragment of claim 2, or a pharmaceutically acceptable salt thereof.

5. The method of claim 4 wherein the mammal is a human being.

6. A method of treating diabetes in a mammal comprising administering to a mammal in need of such treatment an effective amount of a GLP-1 fragment of claim 1, or a pharmaceutically acceptable salt thereof.

7. The method of claim 6 wherein the mammal is a human being.

8. The GLP-1 fragment of claim 1 that has the amino acid sequence:

H₂N-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Arg-Gly-Arg-NH₂ (SEQ ID NO:13).

9. A pharmaceutical composition comprising the GLP-1 fragment of claim 8 in combination with a pharmaceutically acceptable carrier, diluent, or excipient.

10. A method of treating diabetes in a mammal comprising administering to a mammal in need of such treatment an effective amount of the GLP-1 fragment of claim 8, or a pharmaceutically acceptable salt thereof.

11. The method of claim 10 wherein the mammal is a human being.

12. The GLP-1 fragment of claim 1 that has the amino acid sequence:

H₂N-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-OH (SEQ ID NO:10).

13. A pharmaceutical composition comprising the GLP-1 fragment of claim 12 in combination with a pharmaceutically acceptable carrier, diluent, or excipient.

14. A method of treating diabetes in a mammal comprising administering to a mammal in need of such treatment an effective amount of the GLP-1 fragment of claim 12, or a pharmaceutically acceptable salt thereof.

15. The method of claim 14 wherein the mammal is a human being.

16. The GLP-1 fragment of claim 1 that has the amino acid sequence:

H₂N-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-NH₂ (SEQ ID NO:11).

17. A pharmaceutical composition comprising the GLP-1 fragment of claim 16 in combination with a pharmaceutically acceptable carrier, diluent, or excipient.

18. A method of treating diabetes in a mammal comprising administering to a mammal in need of such treatment an effective amount of the GLP-1 fragment of claim 16, or a pharmaceutically acceptable salt thereof.

19. The method of claim 18 wherein the mammal is a human being.

20. A pharmaceutical composition comprising a GLP-1 fragment of claim 1 in combination with a pharmaceutically acceptable carrier, diluent, or excipient.

21. A method of treating diabetes in a mammal comprising administering to a mammal in need of such treatment an effective amount of a GLP-1 fragment having the amino acid sequence:

(SEQ ID NO: 12)
H₂N—Ala—Glu—Gly—Thr—Phe—Thr—Ser—Asp—Val—Ser—Ser—Tyr—Leu—Glu—Gly—Gln—Ala—Ala—Lys—Glu—Phe—Ile—Ala—Trp—Leu—Val—Lys—Gly—Arg—Gly—OH.

22. The method of claim 21 wherein the mammal is a human being.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
      ( A ) LENGTH: 19 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Modified-site
      ( B ) LOCATION: 17..18
      ( D ) OTHER INFORMATION: /note="AA17 is Lys or Arg"

( x i ) SEQUENCE DESCRIPTION: SEQ ID NO:1:

Ser Tyr Leu Glu Gly Gln Ala Ala Lys Glu Phe Ile Ala Trp Leu Val
   1               5                   10                  15

Xaa Gly Arg ( 2 ) INFORMATION FOR SEQ ID NO:2:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:2:

Ser Asp Val Ser
   1

( 2 ) INFORMATION FOR SEQ ID NO:3:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:3:

Thr Ser Asp Val Ser
   1               5

( 2 ) INFORMATION FOR SEQ ID NO:4:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:4:

Phe Thr Ser Asp Val Ser
   1               5

( 2 ) INFORMATION FOR SEQ ID NO:5:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:5:

Thr Phe Thr Ser Asp Val Ser
1               5

( 2 ) INFORMATION FOR SEQ ID NO:6:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:6:

Gly Thr Phe Thr Ser Asp Val Ser
1               5

( 2 ) INFORMATION FOR SEQ ID NO:7:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:7:

Glu Gly Thr Phe Thr Ser Asp Val Ser
1               5

( 2 ) INFORMATION FOR SEQ ID NO:8:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:8:

Ala Glu Gly Thr Phe Thr Ser Asp Val Ser
1               5                   10

( 2 ) INFORMATION FOR SEQ ID NO:9:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 27..28
    ( D ) OTHER INFORMATION: /note="C-terminal amide"

( x i ) SEQUENCE DESCRIPTION: SEQ ID NO:9:

```
        Glu  Gly  Thr  Phe  Thr  Ser  Asp  Val  Ser  Ser  Tyr  Leu  Glu  Gly  Gln  Ala
        1                  5                         10                        15

Ala  Lys  Glu  Phe  Ile  Ala  Trp  Leu  Val  Lys  Gly  Arg
                           20                        25
```

( 2 ) INFORMATION FOR SEQ ID NO:10:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:10:

```
        Glu  Gly  Thr  Phe  Thr  Ser  Asp  Val  Ser  Ser  Tyr  Leu  Glu  Gly  Gln  Ala
        1                  5                         10                        15

Ala  Lys  Glu  Phe  Ile  Ala  Trp  Leu  Val  Lys  Gly  Arg  Gly
                           20                        25
```

( 2 ) INFORMATION FOR SEQ ID NO:11:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 28..29
    ( D ) OTHER INFORMATION: /note="C-terminal amide"

( x i ) SEQUENCE DESCRIPTION: SEQ ID NO:11:

```
        Ala  Glu  Gly  Thr  Phe  Thr  Ser  Asp  Val  Ser  Ser  Tyr  Leu  Glu  Gly  Gln
        1                  5                         10                        15

Ala  Ala  Lys  Glu  Phe  Ile  Ala  Trp  Leu  Val  Lys  Gly  Arg
                           20                        25
```

( 2 ) INFORMATION FOR SEQ ID NO:12:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:12:

```
        Ala  Glu  Gly  Thr  Phe  Thr  Ser  Asp  Val  Ser  Ser  Tyr  Leu  Glu  Gly  Gln
        1                  5                         10                        15

Ala  Ala  Lys  Glu  Phe  Ile  Ala  Trp  Leu  Val  Lys  Gly  Arg  Gly
                           20                        25                        30
```

( 2 ) INFORMATION FOR SEQ ID NO:13:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: peptide ( i x ) FEATURE:

(A) NAME/KEY: Modified-site
(B) LOCATION: 27..28
(D) OTHER INFORMATION: /note="C-terminal amide"

(xi) SEQUENCE DESCRIPTION: SEQ ID NO:13:

```
Glu Gly Thr Phe Thr Ser Asp Val Ser Ser Tyr Leu Glu Gly Gln Ala
1               5                   10                  15
Ala Lys Glu Phe Ile Ala Trp Leu Val Arg Gly Arg
            20                  25
```